(12) United States Patent  
Collins

(10) Patent No.: US 7,070,327 B2  
(45) Date of Patent: Jul. 4, 2006

(54) FOCUSED RADIATION VISUALIZATION

(75) Inventor: William F. Collins, Clayton, CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 143 days.

(21) Appl. No.: 10/253,287

(22) Filed: Sep. 24, 2002

(65) Prior Publication Data

US 2003/0206613 A1 Nov. 6, 2003

Related U.S. Application Data

(60) Provisional application No. 60/377,352, filed on May 1, 2002.

(51) Int. Cl.
*A61B 6/08* (2006.01)
(52) U.S. Cl. ........................................ 378/206; 378/84
(58) Field of Classification Search ................ 378/84, 378/206, 64, 65, 147, 205, 85; 359/845
See application file for complete search history.

(56) References Cited

U.S. PATENT DOCUMENTS

| | | | |
|---|---|---|---|
| 1,865,441 A | 7/1932 | Mutscheller | |
| 2,557,662 A | 6/1951 | Kirkpatrick | |
| 4,256,966 A | 3/1981 | Heinz | |
| 4,940,319 A * | 7/1990 | Ueda et al. ............... | 359/853 |
| 5,142,559 A | 8/1992 | Wielopolski | |
| 5,220,169 A * | 6/1993 | Ninomiya et al. ........ | 250/358.1 |
| 5,438,991 A | 8/1995 | Wong et al. | |
| 5,604,782 A | 2/1997 | Cash, Jr. | |
| 5,661,773 A | 8/1997 | Swerdloff et al. | |
| 5,761,256 A | 6/1998 | Inoue et al. | |
| 5,778,043 A | 7/1998 | Cosman | |
| 5,870,697 A | 2/1999 | Chandler et al. | |
| 6,125,164 A | 9/2000 | Murphy et al. | |
| 6,125,295 A | 9/2000 | Cash, Jr. et al. | |
| 6,144,875 A | 11/2000 | Schweikard | |
| 6,195,410 B1 | 2/2001 | Cash, Jr. | |
| 6,359,963 B1 | 3/2002 | Cash | |
| 6,366,801 B1 * | 4/2002 | Cash et al. ............... | 600/431 |
| 6,389,100 B1 * | 5/2002 | Verman et al. ............ | 378/84 |
| 6,516,046 B1 | 2/2003 | Frohlich et al. | |
| 6,535,574 B1 | 3/2003 | Collins et al. | |
| 6,750,435 B1 * | 6/2004 | Ford ........................ | 250/201.2 |
| 6,754,304 B1 | 6/2004 | Kumakhov | |
| 6,782,073 B1 | 8/2004 | Collins | |
| 6,817,762 B1 * | 11/2004 | Proksa ....................... | 378/206 |
| 2001/0043667 A1 | 11/2001 | Antonell et al. | |

(Continued)

FOREIGN PATENT DOCUMENTS

DE 10 139 934 3/2003

(Continued)

OTHER PUBLICATIONS

"Highly Oriented Pyrolytic Graphite", download from http://www.win.ne.jp/~techno/e_HOPG.html on Jul. 29, 2002. 1pg.

(Continued)

*Primary Examiner*—David V. Bruce
*Assistant Examiner*—Hoon Song

(57) ABSTRACT

A system includes substantial focus of radiation on a focal area, the focused radiation following a radiation path from a lens to the focal area, and projection of light on a surface so as to substantially indicate an intersection of the radiation path with the surface. In some aspects, the light projected on the surface substantially indicates a distance between the surface and the focal area.

30 Claims, 6 Drawing Sheets

U.S. PATENT DOCUMENTS

2002/0044626 A1     4/2002    Joensen et al.
2002/0085668 A1     7/2002    Blumhofer
2003/0206613 A1    11/2003    Collins

FOREIGN PATENT DOCUMENTS

EP          1 195 177 A1     4/2002
GB         2 371 1964 A      8/2002
WO      WO 02/22019       3/2002

OTHER PUBLICATIONS

"Overview of Cancer and Radiation Therapy", download from http://www.vetradtherapy.com/overview.html on Jul. 24, 2002. 6pgs.

Graham P.A., et al., "Dynamic Surface, Matching for Patient Positioning in Radiotherapy," Information Visualization, Jul. 29, 1998, pp. 16-24, XP010292559.

* cited by examiner

FOCUSED RADIATION VISUALIZATION

CROSS-REFERENCE TO RELATED APPLICATIONS

This application claims priority to U.S. Provisional Application No. 60/377,352, filed May 1, 2002 and entitled "System and Method of Focused Orthovoltage Technology for Radiotherapy".

BACKGROUND

1. Field

The present invention relates generally to medical treatment using focused radiation, and more particularly to planning and/or verification systems used in conjunction with such treatment.

2. Description

Conventional radiation treatment typically involves directing a radiation beam at a tumor located within a patient. The radiation beam is intended to deliver a predetermined dose of treatment radiation to the tumor according to an established treatment plan. The goal of such treatment is to kill tumor cells with ionizations caused by the radiation.

Healthy tissue and organs are often in the treatment path of the radiation beam during radiation treatment. The healthy tissue and organs must be taken into account when delivering a dose of radiation to the tumor, thereby complicating determination of the treatment plan. Specifically, the plan must strike a balance between the need to minimize damage to healthy tissue and organs and the need to ensure that the tumor receives an adequately high dose of radiation. In this regard, cure rates for many tumors are a sensitive function of the radiation dose they receive.

Radiation treatment plans are designed to maximize radiation delivered to a target while minimizing radiation delivered to healthy tissue. However, even if such a plan is designed, the goals of maximizing target radiation and minimizing healthy tissue radiation may not be achieved if the radiation is not delivered exactly as required by the treatment plan. More specifically, radiation delivery errors as well as poor treatment planning can result in low irradiation of tumors and high irradiation of sensitive healthy tissue.

A kilovoltage radiation treatment system such as those described in U.S. Pat. No. 6,366,801 to Cash et al produces a divergent beam of traditional medical x-rays having energies in the 50 to 150 keV range and focuses the beam on a target using a lens designed for this purpose. Conventional systems for accurately delivering such a beam to a target are not satisfactorily efficient.

SUMMARY

To address at least the foregoing, some embodiments of the present invention provide a system, method, apparatus, and means to substantially focus radiation on a focal area, the focused radiation following a radiation path from a lens to the focal area, and project light on a surface so as to substantially indicate an intersection of the radiation path with the surface.

In other aspects, light is projected on a surface so as to substantially indicate an intersection of focused radiation to be delivered with the surface. Further to this aspect, the light projected on the surface may substantially indicate a distance between the surface and a focal area on which the radiation is focused.

In still other aspects, a radiation-focusing lens is provided which includes at least one radiation-focusing element for substantially focusing radiation on a focal area, the focused radiation to follow a radiation path from the lens to the focal area, and at least one light-emitting element for projecting light on a surface so as to substantially indicate an intersection of the radiation path with the surface.

Some embodiments of the invention may include a radiation source for emitting radiation, a radiation-focusing lens to substantially focus the radiation on a focal area, the focused radiation to follow a radiation path from the lens to the focal area, and at least one light-emitting element to project light on a surface so as to substantially indicate an intersection of the radiation path with the surface.

According to some embodiments, a path of radiation to exit from a radiation-focusing lens is determined, optical elements are configured to project light substantially delineating the radiation path, and the light is projected on a surface so as to substantially indicate an intersection of the radiation path with the surface.

In some embodiments, at least one light-emitting element is provided to project light on a surface so as to substantially indicate an intersection of a convergent radiation path with the surface.

The present invention is not limited to the disclosed embodiments, however, as those of ordinary skill in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts, and wherein.

DETAILED DESCRIPTION

The following description is provided to enable any person of ordinary skill in the art to make and use the invention and sets forth the best modes contemplated by the inventor for carrying out the invention. Various modifications, however, will remain readily apparent to those in the art.

Figure 1:
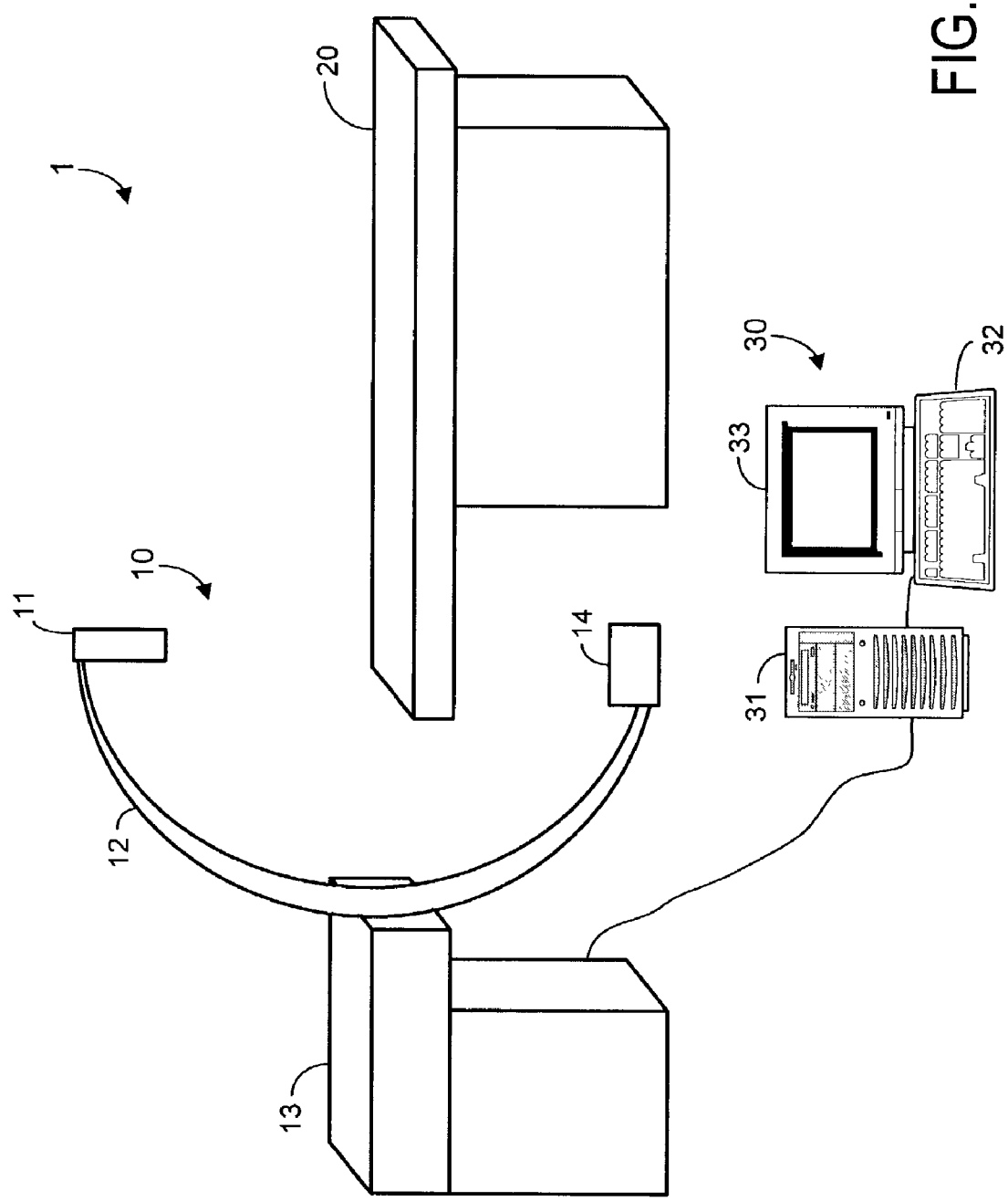
FIG. 1 is a diagram illustrating a radiation treatment room according to some embodiments of the present invention.

FIG. 1 illustrates radiation treatment room 1 pursuant to some embodiments of the present invention. Radiation treatment room 1 includes kilovoltage radiation treatment unit 10, treatment table 20 and operator station 30. The elements of radiation treatment room 1 are used to deliver kilovoltage radiation to a patient according to a treatment plan. In this regard, kilovoltage radiation refers herein to any radiation having energies ranging from 50 to 150 keV. However, it should be noted that some embodiments of the present invention may be used in conjunction with any focused radiation beam.

Treatment unit 10 is used to deliver treatment radiation to a treatment area and includes treatment head 11, c-arm 12, base 13 and imaging system 14. Treatment head 11 includes a beam-emitting device such as an x-ray tube for emitting kilovoltage radiation used during calibration and/or treatment. The radiation may comprise electron, photon or any other type of radiation. Treatment head 11 also includes a cylinder in which are disposed elements such as a focusing lens for optically processing the emitted radiation and light-emitting elements for projecting light in accordance with some embodiments of the invention. Treatment head 11 will be described in more detail below with respect to FIG. 2.

C-arm 12 is slidably mounted on base 13 and can therefore be moved in order to change the position of treatment head 11 with respect to table 20. In some embodiments, base 13 also includes a high-voltage generator for supplying power used by treatment head 11 to generate kilovoltage radiation. Many c-arm/base configurations may be used in conjunction with some embodiments of the present invention, including configurations in which base 13 is rotatably mounted to a ceiling of room 1, configurations in which one c-arm is slidably mounted on another c-arm, and configurations incorporating multiple independent c-arms.

Examples of c-arm kilovoltage radiation units include Siemens SIREMOBIL™, MULTISTAR™, BICOR™ and POLYSTAR™ units as well as other units designed to perform tomography and/or angiography. These units are often less bulky and less costly than megavoltage radiation systems. Of course, any system for delivering a focused radiation beam may be used in conjunction with some embodiments of the present invention.

Imaging system 14 produces an image based on the radiation emitted by treatment head 11. The image reflects the attenuative properties of objects located between treatment head 11 and imaging system 14 while the radiation is emitted. Imaging system 14 may comprise an image intensifier and a camera. An image intensifier is a vacuum tube that converts X-rays to visible light, which is then detected by the camera to produce an image. Imaging system 14 may also comprise a flat-panel imaging system that uses a scintillator and silicon sensor elements or direct x-ray conversion detectors to produce an image based on received radiation.

A patient is placed on treatment table 20 during treatment in order to position a target area between treatment head 11 and imaging system 14. Accordingly, table 20 may comprise suitable electrical and/or mechanical systems for moving itself with respect to unit 10.

Operator station 30 includes processor 31 in communication with an input device such as keyboard 32 and an output device such as operator display 33. Operator station 30 is typically operated by an operator who administers actual delivery of radiation treatment as prescribed by an oncologist. Operator station 30 may be located apart from treatment unit 10, such as in a different room, in order to protect the operator from radiation. It should be noted, however, that kilovoltage radiation treatment does not require protective measures to the extent of those taken during megavoltage radiation therapy, resulting in less costly therapy.

Processor 31 may store processor-executable process steps according to some embodiments of the present invention. In some aspects, the process steps are executed by operator station 30, imaging system 14, other elements of treatment unit 10, and/or another device to focus radiation on a focal area, the focused radiation substantially following a radiation path from a lens to the focal area, and to project light on a surface so as to indicate an intersection of the radiation path with the surface.

The process steps may also be executed to determine a path of radiation to exit from a radiation-focusing lens, to configure elements to project light substantially delineating the radiation path, and to project the light on a surface so as to indicate an intersection of the radiation path with the surface.

The above-described steps may also be embodied, in whole or in part, by hardware and/or firmware of processor 31, treatment head 11, imaging system 14, other elements of treatment unit 10, and another device. Of course, each of the devices shown in FIG. 1 may include less or more elements than those shown. In addition, embodiments of the invention are not limited to the devices shown.

Figure 2:
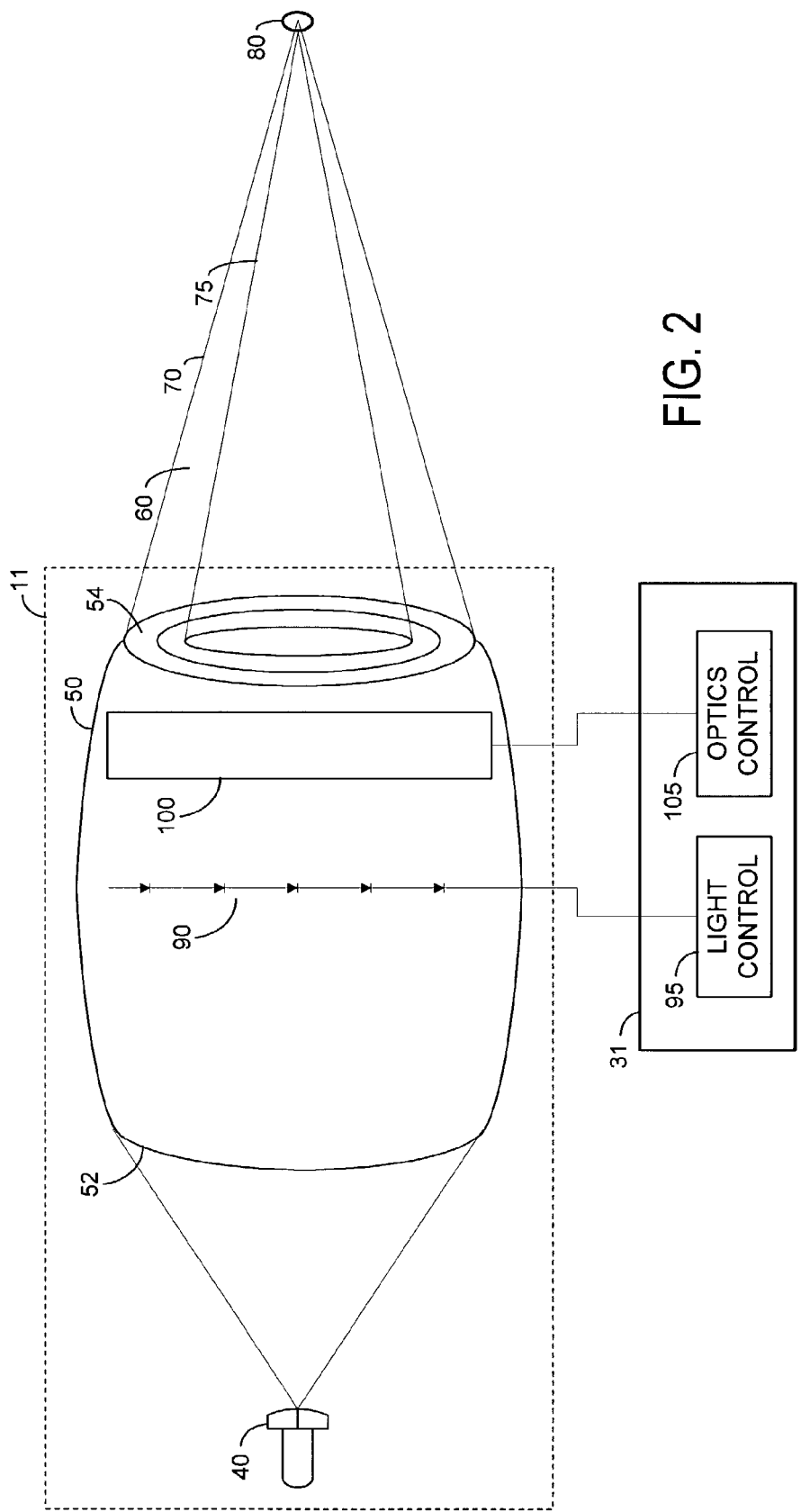
FIG. 2 is a diagram illustrating a radiation-focusing lens according to some embodiments of the present invention.

FIG. 2 is a representative view of elements of treatment head 11 according to some embodiments of the present invention. Neither the elements nor their physical relationships to one another are necessarily drawn to scale. As shown, treatment head 11 includes x-ray tube 40 for emitting radiation toward lens 50. In some embodiments, x-ray tube 40 comprises a Diabolo™ x-ray tube. The radiation enters entry surface 52 of lens 50 and some or all of the radiation exits exit surface 54. In this regard, the radiation energy exiting exit surface 54 may comprise 10% or less of the total radiation energy striking entry surface 52.

Figure 4:
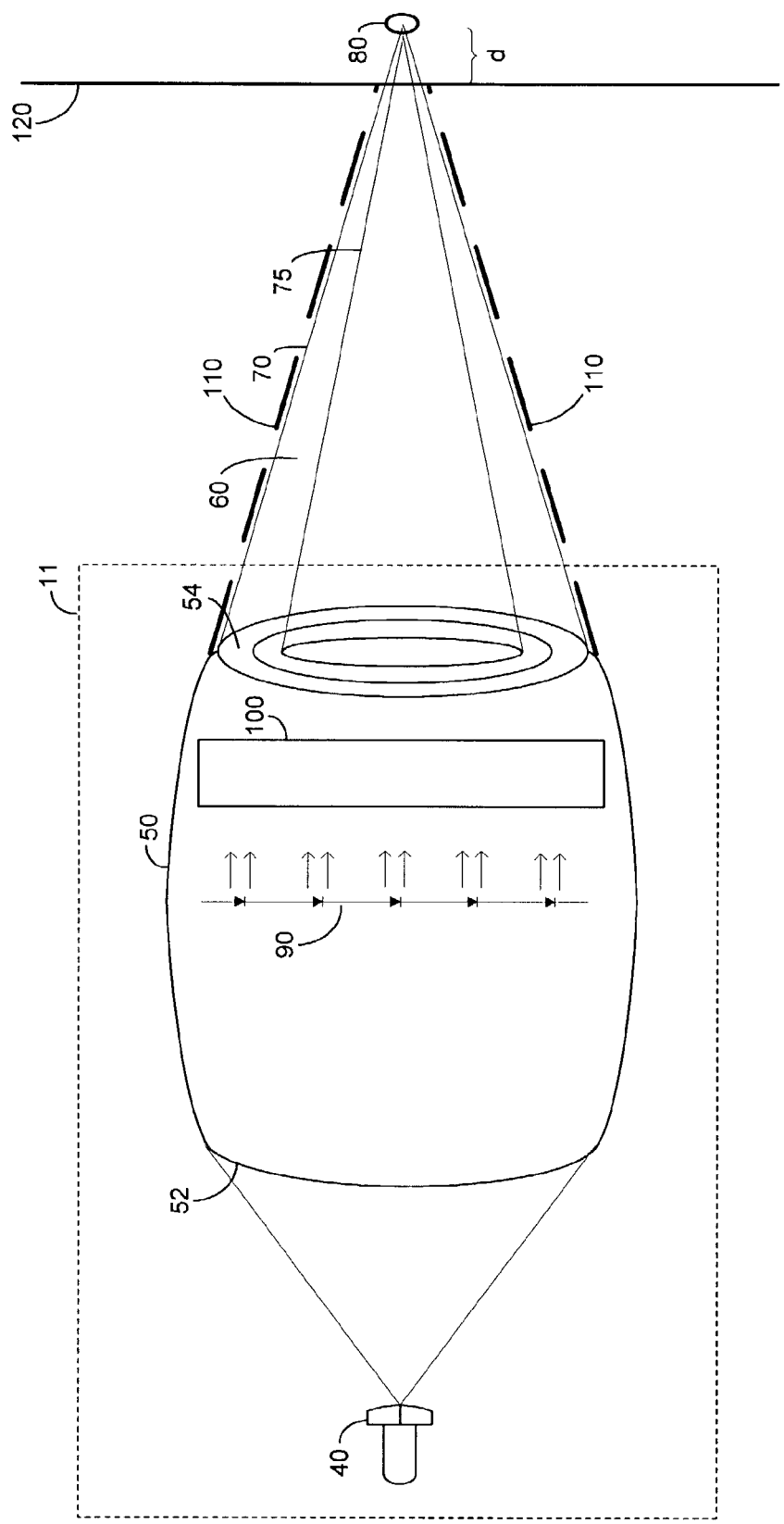
FIG. 4 is a diagram illustrating light projection according to some embodiments of the present invention.

Lens 50 may comprise any radiation-focusing lens, including those having a shape different from that illustrated. In this regard, lens 50 of FIG. 2 comprises thin strips of reflective material arranged in the form of several barrels nested around a central axis. Each "barrel" is separated from adjacent "barrels" by Plexiglas or another optically neutral substrate. The strips of reflected material are represented in FIG. 4 by the elliptical lines on exit surface 54, while the empty areas between the elliptical lines represent the substrate. Lens 50 may also comprise any other radiation-focusing lenses such as those described in U.S. Pat. No. 6,359,963 to Cash, in U.S. Pat. No. 5,604,782 to Cash, Jr., in U.S. Patent Application Publication No. 2001/0043667 of Antonell et al., and/or elsewhere in currently or hereafter-known art.

Highly Oriented Pyrolitic Graphite (HOPG) may be used as the reflective material of lens 50. HOPG consists of planes of carbon atoms that are highly oriented toward one another. In the ideal variant, these planes are parallel to one another.

By virtue of the composition, shape and construction of lens 50 and of properties of the radiation emitted by x-ray tube 40, radiation exiting from exit surface 54 substantially follows radiation path 60. Geometrically, path 60 comprises a hollow conical volume between outer cone surface 70 and inner cone surface 75. Of course, different radiation-focusing lenses used in conjunction with embodiments of the invention may direct radiation along differently-shaped paths.

Lens 50 operates to substantially focus all or a portion of the directed radiation on focal area 80. Focal area 80 may comprise a tightly-focused area (e.g., a point in space) or a larger area. In some embodiments of lens 50, focal area 80 is approximately 1 cm in diameter. According to the FIG. 2 embodiment, focal area 80 is spaced from an exit surface of lens 50 by a distance determined by the composition, shape and construction of lens 50 as well as by characteristics of the radiation emitted by x-ray tube 40.

Path 60 might not terminate at focal area 80. Rather, path 60 may continue thereafter, becoming further attenuated and unfocused as its distance from focal area 80 increases. In some embodiments, the divergence of path 60 from focal area 80 roughly mirrors its convergence thereto.

Laser diodes 90 are light-emitting elements mounted on and/or within lens 50. Accordingly, laser diodes 90 are not limited to the physical arrangement illustrated in FIG. 2. For example, laser diodes 90 may be embedded within the Plexiglas volumes of lens 50 in a manner that allows lens 50 to maintain an ability to focus radiation. Laser diodes 90 may also be mounted to the outer surface of lens 50. Such a mounting may be particularly suitable in a case that lens 50 relies entirely on internal reflections to focus incoming radiation. Generally, laser diodes 90 may be arranged in any manner that allows operation in accordance with embodiments of the present invention.

Laser diodes 90 are used to project light in accordance with some embodiments of the invention. More particularly, laser diodes 90 may be used to project light on a surface so as to substantially indicate an intersection of a radiation path with the surface. The projected light may indicate a distance between the surface and a focal area associated with the radiation path. In some embodiments, the projected light substantially delineates a three-dimensional surface of the radiation path. These and other features will be described in more detail below.

The light generated by laser diodes 90 may be projected while radiation is being emitted by x-ray tube 40 and is following the radiation path and/or while no radiation is being delivered, e.g., during treatment planning or verification of treatment head position. Also, some embodiments of the invention may use one or more types of light-emitting elements other than laser diodes, including at least non-laser light-emitting diodes, fiber optic elements, incandescent light-emitting elements, and fluorescent light-emitting elements.

Laser diodes 90 may be controlled by light control 95 of processor 31. Light control 95 may comprise one or more of software, hardware, and firmware elements to control laser diodes 90 to operate according to some embodiments of the invention. Of course, light control 95 may be located in other devices, such as treatment head 11, base 13, a stand-alone device, or another device.

Optics 100 may assist in projecting the light emitted by laser diodes 90 according to some embodiments of the invention. Optics 100 may comprise one or more lenses, mirrors and/or other optical devices for directing light emitted by laser diodes 90. Optics 100 may be controlled by optics control 105 to project light as desired. As described above with respect to light control 95, optics control 105 may be located in processor 31, treatment head 11, base 13, a stand-alone device, or another device.

Treatment head 11 may also include beam-shaping devices such as one or more jaws, collimators, reticles and apertures. These devices may be used to change the shape of path 60 and to thereby also change the shape and/or position of focal area 80. The devices may be placed between lens 50 and focal area 80 and/or between x-ray tube 40 and lens 50.

Figure 3:
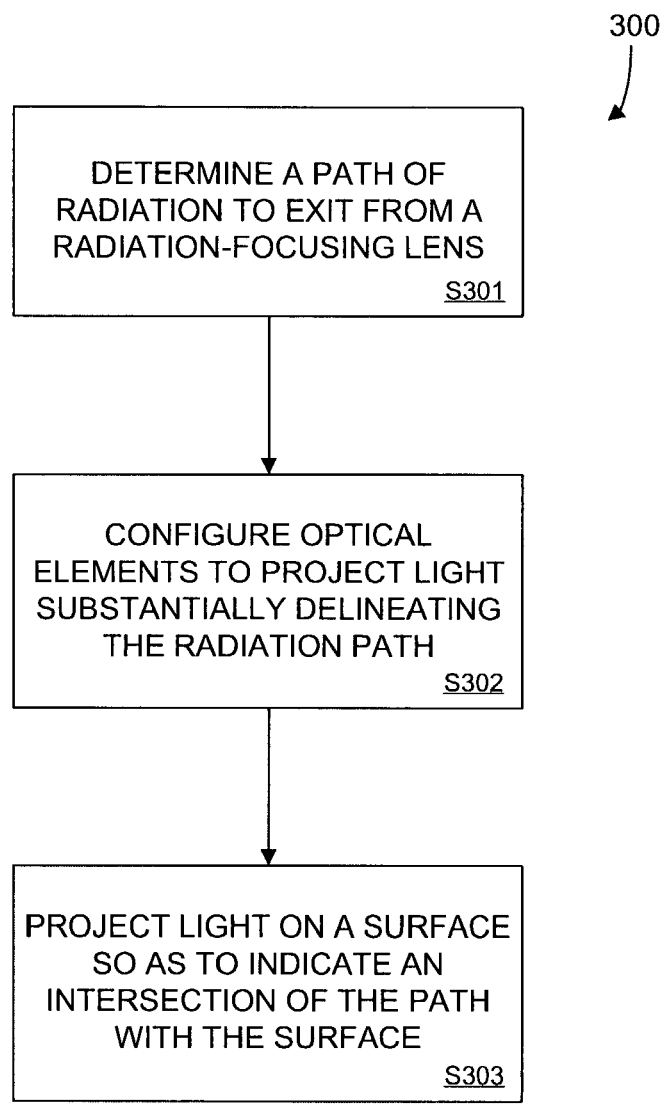
FIG. 3 comprises a flow diagram illustrating process steps according to some embodiments of the present invention.

FIG. 3 comprises a flow diagram of process steps 300 to project a visualization of a radiation path according to some embodiments of the invention. Process steps 300 may be embodied by hardware and/or software of processor 31, treatment unit 10, and/or another device in direct or indirect communication with laser diodes 90.

Process steps 300 begin at step S301, in which a radiation path is determined. In this regard, process steps 300 may be executed during the planning or verification of future radiation treatment and therefore the determined radiation path may be a path followed by planned, rather than actual, radiation. As shown in FIG. 2, the path may be a path of radiation to exit an exit surface of a radiation-focusing lens.

In the present example, the determined path of radiation is path 60 of radiation exiting exit surface 54. Path 60 may be determined based on an energy and type of radiation to be transmitted by tube 40, characteristics of lens 50 and other factors known in the art. According to some embodiments, path 60 is determined by performing ray tracing from a location of focal area 80 to exit surface 54. In some embodiments, a size and location of path 60 with respect to lens 50 is determined in step S301.

Next, in step S302, optical elements are configured to project light that substantially delineates the path determined in step S301. The configured optical elements may include one or more laser diodes 90 and may also include one or more of the elements of optics 100. In some embodiments, light control 95 and optics control 105 operate in step S302 to configure the optical elements based on data representing the path that was determined in step S301.

It should be noted that steps S301 and S302 may be performed during manufacture of lens 50. Specifically, optical elements of lens 50 may be configured during its manufacture to project light that substantially delineates a path of radiation that will result from the use of lens 50. Steps S301 and S302 may also be performed during periodic calibration procedures.

In step S303, light is projected on a surface so as to substantially indicate an intersection of the radiation path with the surface. FIG. 4 illustrates some embodiments of step S303. As shown, laser diodes 90 emit light toward optics 100, which in turn project light 110 on surface 120. Some embodiments do not include optics 100. Accordingly, both laser diodes 90 and optics 100 can be seen as projecting light 110 on surface 120 so as to indicate an intersection of radiation path 60 with surface 120.

Surface 120 is positioned in FIG. 4 between lens 50 and focal area 80. FIG. 4 represents a scenario in which a radiation target lies within a volume (e.g., a patient's body) having surface 120 at a distance d below surface 120. As shown in FIG. 4, light 110 delineates outer surface 70 of radiation path 60.

Figure 5A:
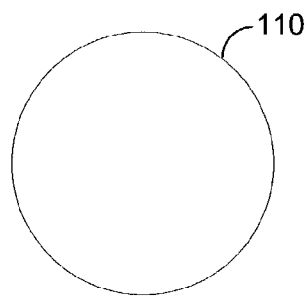
FIGS. 5a through 5f are views illustrating light projected on a surface so as to indicate an intersection of a radiation path with the surface according to some embodiments of the present invention.
Figure 5B:
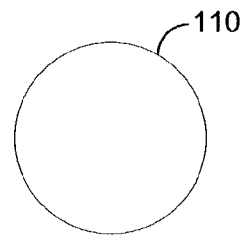

FIG. 5a is a view of light 110 as projected on surface 120 so as to indicate an intersection of path 60 with surface 120. Light 110 of FIG. 5a comprises a circular ring because surface 120 is perpendicular to a central axis of outer surface 70. FIG. 5b illustrates a case in which surface 120 remains perpendicular to a central axis of outer surface 70 and between lens 50 and focal area 80, but in which distance d between focal area 80 and surface 120 is greater than that shown in FIG. 4. As shown in FIG. 5b, the circular ring of light 110 projected on surface 120 decreases in size because the cross-sectional size of outer surface 70 at the new position of surface 120 is smaller in the new case. As a result, an area delineated by light 110 projected on surface 120 indicates a value of distance d between surface 120 and focal area 80. In some embodiments, the area is indirectly proportional to a distance between surface 120 and focal area 80.

Light 110 may also delineate inner surface 75 of path 60. In such a case, the light projected on surface 120 may show two concentric circles, with the area between the circles indicating an intersection of path 60 with surface 120. Of course, light 120 may only delineate inner surface 75.

Figure 5C:
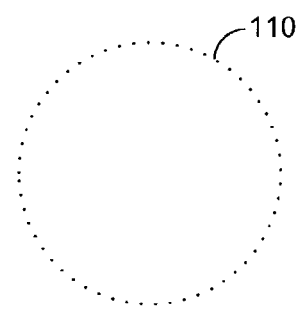
Figure 5D:
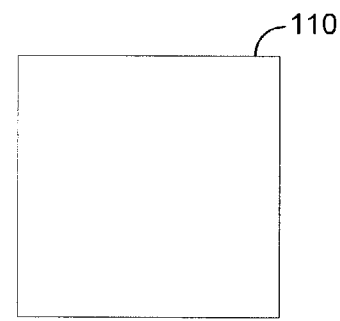

FIGS. 5c through 5f illustrate light projected on a surface so as to indicate an intersection of a radiation path with the surface according to some embodiments of the invention. For example, the circular ring of FIG. 5c illustrates some embodiments in which light projected by laser diodes 90 and/or optics 100 is not continuous. In some embodiments, optics 100 operate to receive light 110 as shown in FIG. 5c and to project it to create projected light as shown in FIG. 5a.

Figure 5E:
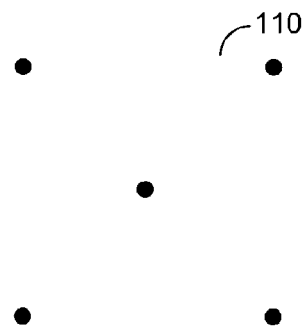
Figure 5F:
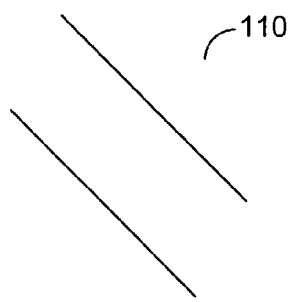

Light 110 of FIG. 5e is also discontinuous, yet an area delineated thereby may indicate an intersection of path 60 with surface 120. In this regard, the area may indicate an intersection comprising a square area encompassing each light element of FIG. 5e, or an intersection comprising only those areas illuminated by the five light points of FIG. 5e. Of course, other intersections may be indicated by light 110 of FIG. 5e. Similarly, an area delineated by light 110 of FIG. 5f may indicate any intersection. Moreover, the respective areas delineated by light 110 of FIG. 5e and FIG. 5f may decrease as surface 120 is moved relatively closer to focal area 80.

Figure 6:
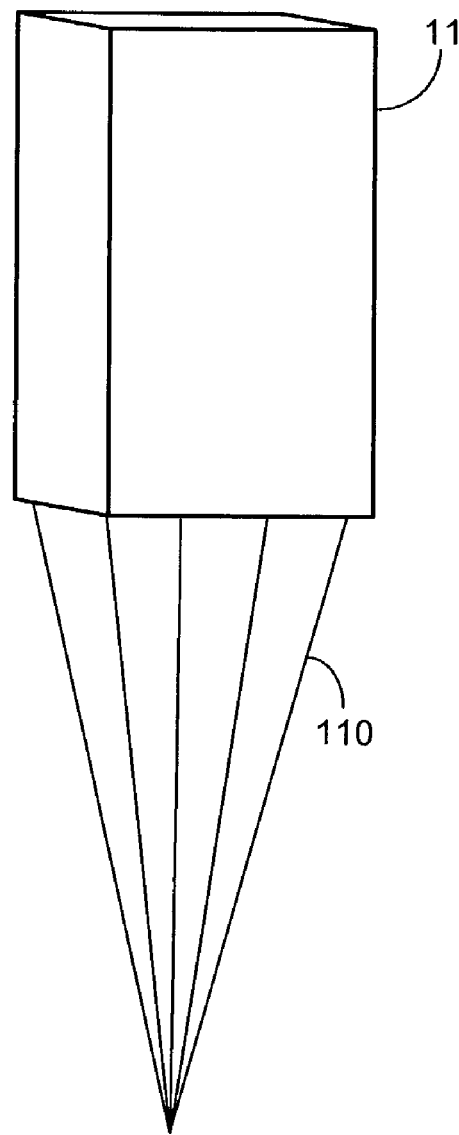
FIG. 6 is a view illustrating projected light substantially delineating a three-dimensional radiation path according to some embodiments of the present invention.

FIG. 6 illustrates treatment head 11 and light 120 projected from laser diodes 90 and/or optics 100. As shown, light 120 substantially delineates a three-dimensional outer surface of path 60. Such a projection may allow an operator to visualize the entire volume of path 60 from treatment head 11 to a surface intercepted by path 60. In some embodiments, light 120 also or alternatively delineates a three-dimensional inner surface of path 60. In order to delineate a three-dimensional surface of path 60, light 120 may consist of individual beams spaced along the perimeter of path 60 as shown or a solid cone of light enveloping path 60. Of course, other schemes for projecting light so as to substantially delineate a three-dimensional surface of a radiation path may be used in conjunction with embodiments of the invention.

Those in the art will appreciate that various adaptations and modifications of the above-described embodiments can be configured without departing from the scope and spirit of the invention. Therefore, it is to be understood that, within the scope of the appended claims, the invention may be practiced other than as specifically described herein.

What is claimed is:

1. An apparatus comprising:
   a radiation-focusing lens to substantially focus x-rays on a focal area, the focused x-rays to follow a radiation path from the lens to the focal area; and
   at least one light-emitting element embedded within the radiation-focusing lens for projecting light to substantially delineate the radiation path.

2. An apparatus according to claim 1, wherein the at least one light-emitting element is further to project light on a surface to substantially indicate an intersection of the radiation path with the surface.

3. An apparatus according to claim 2, wherein the surface is located between the lens and the focal area.

4. An apparatus according to claim 2, wherein the light projected on the surface substantially indicates a distance between the surface and the focal area.

5. An apparatus according to claim 4, wherein an area of the projected light on the surface in a case that the surface is at a first location is greater than in a case that the surface is at a second location, wherein the first location and the second location are between the lens and the focal area, and wherein the second location is closer to the focal area than the first location.

6. An apparatus according to claim 1, wherein the at least one light-emitting element projects light tat substantially delineates a three-dimensional outer surface of the radiation path.

7. An apparatus according to claim 6, wherein the at least one light-emitting element projects light that substantially delineates a three-dimensional inner surface of the radiation path.

8. An apparatus according to claim 1, wherein the at least one light-emitting element projects light that substantially delineates a three-dimensional inner surface of the radiation path.

9. An apparatus according to claim 1, further comprising optics for projecting the light on the surface.

10. A lens according to claim 1, wherein the focused x-rays comprise treatment radiation.

11. A method comprising:
    operating at least one light-emitting element embedded within a radiation-focusing lens to project light to substantially delineate a radiation path; and
    substantially focusing x-rays along the radiation path using the radiation-focusing lens,
    wherein the projected light substantially delineates a three-dimensional inner surface of the radiation path.

12. A method according to claim 11, wherein projecting the light comprises projecting light on a surface to substantially indicate an intersection of the radiation path with the surface.

13. A method according to claim 12, wherein the surface is located between the lens and a focal area.

14. A method according to claim 12, wherein the light projected on the surface indicates a distance between the surface and a focal area.

15. A method according to claim 14, wherein an area of the projected light on the surface in a case that the surface is at a first location is greater than in a case that the surface is at a second location, wherein the first location and the second location are between the lens and the focal area, and wherein the second location is closer to the focal area than the first location.

16. A method according to claim 11, wherein the projected light substantially delineates a three-dimensional outer surface of the radiation path.

17. A method according to claim 11, wherein the operating step comprises controlling optics to project the light on the surface.

18. A method according to claim 11, wherein the focused x-rays comprise treatment radiation.

19. A method comprising:
    determining a path of x-rays to exit from a radiation-focusing lens;
    configuring at least one light-emitting element embedded within the radiation-focusing lens to project light substantially delineating the x-ray path; and
    projecting the light on a surface so as to substantially indicate an intersection of the x-ray path with the surface.

20. A method according to claim 19, wherein the light projected on the surface substantially indicates a distance between the surface and a focal area on which the x-ray path is focused.

21. A method according to claim 19, wherein an area of the projected light on the surface in a case that the surface is at a first location is greater than in a case that the surface is at a second location, wherein the first location and the second location are between a lens used to focus the radiation and the focal area, and wherein the second location is closer to the focal area than the first location.

22. A method according to claim 19, further comprising projecting light that substantially delineates a three-dimensional inner surface of the radiation path.

23. A method according to claim 22, further comprising projecting light that substantially delineates a three-dimensional outer surface of the radiation path.

24. A method according to claim 19, wherein the x-rays comprise treatment radiation.

25. A computer-readable medium storing computer-executable process steps, the process steps comprising
- a step to determine a path of x-rays to exit from a radiation-focusing lens;
- a step to configure at least one light-emitting element embedded within the radiation-focusing lens to project light substantially delineating the x-ray path; and
- a step to project the light on a surface so as to substantially indicate an intersection of the x-ray path with the surface.

26. A medium according to claim 25, wherein the light projected on the surface substantially indicates a distance between the surface and a focal area on which the x-ray path is focused.

27. A medium according to claim 25, wherein an area of the projected light on the surface in a case that the surface is at a first location is greater than in a case that the surface is at a second location, wherein the first location and the second location are between a lens used to focus the radiation and the focal area, and wherein the second location is closer to the focal area than the first location.

28. A medium according to claim 25, the process steps further comprising a step to project light that substantially delineates a three-dimensional inner surface of the x-ray path.

29. A medium according to claim 28, the process steps further comprising a step to project light that substantially delineates a three-dimensional outer surface of the x-ray path.

30. A medium according to claim 25, wherein the x-rays comprise treatment radiation.

* * * * *